(12) United States Patent
Hanna et al.

(10) Patent No.: US 11,053,254 B2
(45) Date of Patent: Jul. 6, 2021

(54) CRYSTALLINE FORMS OF MITOMYCIN C FOR TREATMENT OF CANCER

(71) Applicant: TRANSGENEX NANOBIOTECH, INC., Tampa, FL (US)

(72) Inventors: Mazen Hanna, Tampa, FL (US); Manomi Perera, Tampa, FL (US); Jiyu Yan, Tampa, FL (US); Andrew Hanna, Lutz, FL (US)

(73) Assignee: TRANSGENEX NANOBIOTECH INC., Tampa, FL (US)

( * ) Notice: Subject to any disclaimer, the term of this patent is extended or adjusted under 35 U.S.C. 154(b) by 0 days.

(21) Appl. No.: 16/272,377

(22) Filed: Feb. 11, 2019

(65) Prior Publication Data

US 2019/0248800 A1     Aug. 15, 2019

Related U.S. Application Data

(60) Provisional application No. 62/629,888, filed on Feb. 13, 2018.

(51) Int. Cl.
| | |
|---|---|
| *C07D 487/14* | (2006.01) |
| *A61P 35/00* | (2006.01) |
| *A61K 31/407* | (2006.01) |

(52) U.S. Cl.
CPC .......... *C07D 487/14* (2013.01); *A61K 31/407* (2013.01); *A61P 35/00* (2018.01); *C07B 2200/13* (2013.01)

(58) Field of Classification Search
CPC ............... A61K 31/407; C07D 487/14; C07B 2200/13; A61P 35/00
USPC ................................. 514/410; 548/422, 961
See application file for complete search history.

(56) References Cited

U.S. PATENT DOCUMENTS 5,180,670 A * 1/1993 Iwata ............... B01D 15/325
435/119

FOREIGN PATENT DOCUMENTS

| CN | 102526033 A | * | 7/2012 |
| JP | 2001031680 A | * | 2/2001 |

OTHER PUBLICATIONS

English translation of the Japanese Patent Publication JP-2001031680-A. (Year: 2001).*
Berge, S., L. Bighleyand D. Monkhouse, "Pharmaceutical Salts" J. Pharm. Sci. (1977), 66 (1), pp. 1-19. (Year: 1977).*
Byrn, S., R. Pfeiffer, M. Ganey, C. Hoiberg and G. Poochikian, "Pharmaceutical Solids: A strategic approach to regulatory considerations" Pharmaceutical Research (1995), 12 (7), pp. 945-954. (Year: 1995).*
English translation of the description of the Chinese Patent Publication CN-102526033-A. (Year: 2012).*
English translation of the claims of the Chinese Patent Publication CN-102526033-A. (Year: 2012).*
Elder et al., "use of Pharmaceutical salts and cocrystals to address the issue of poor solubility", International Journal of Pharmaceutics, 453 (2013), pp. 88-100.
Fabian et al., "Cocrystals of fenamic acids with nicotinamide", http://pubs.acs.org/doi/abs/10.1021/cg200429j; ACS, 2011, pp. 1-28.
Karagianni et al., "Pharmaceutical Cocrystals:New Solid Phase Modification Approaches for the Formulation of APIs", Pharmaceutics, 2018, 10,18, pp. 1-30.
Miroshnyk and Mirza "Capturing the Advantages of Co-Crystals", Pharmaceutical Technology, Jul. 1, 2010, pp. 1-8.
Pindelska et al., "Pharmaceutical cocrystals, salts and polymorphs: Advanced characterization techniques", Advanced Drug Delivery Reviews, 117 (2017), pp. 111-146.
Punmalee et al., "Antisolvent Crystallization of Polymorphs of L-Histidine", Chem. Eng. TechnoL, 2018, 41, No. 6, pp. 1132-1138.
Schultheiss and Newman "Pharmaceutical Cocrystals and Their Physiochemical Properties", Cryst. Growth Des., vol. 9, No. 6, 2009; 2950-2967.
G. Patrick Stahly "A Survey of Cocrystals Reported Prior to 2000", Cryst. Growth Des., vol. 9, No. 10, 2009; 4212-4229.
Stanton and Bak "Physicochemical Properties of Pharmaceutical Co-Crystals: A Case Study of Ten AMG 517 Co-Crystals", Cryst. Growth Des., 2008, 8(10); 3856-3862.
Weyna et al., "Syntheis and Structural Characterization of Cocrystals and Pharmaceutical Cocrystals: Mechanochemistry vs Slow Evaporation from Solution", Cryst. Growth Des., vol. 9, No. 2, 2009; 1106-1123.

* cited by examiner

*Primary Examiner* — Joseph R Kosack
*Assistant Examiner* — Sagar Patel
(74) *Attorney, Agent, or Firm* — J.A. Lindeman & Co. PLLC

(57) ABSTRACT

Synthesis and characterization of novel crystalline mitomycin C forms suitable for pharmaceutical compositions in drug delivery systems to treat human or warm-blooded diseases.

31 Claims, 14 Drawing Sheets
(14 of 14 Drawing Sheet(s) Filed in Color)

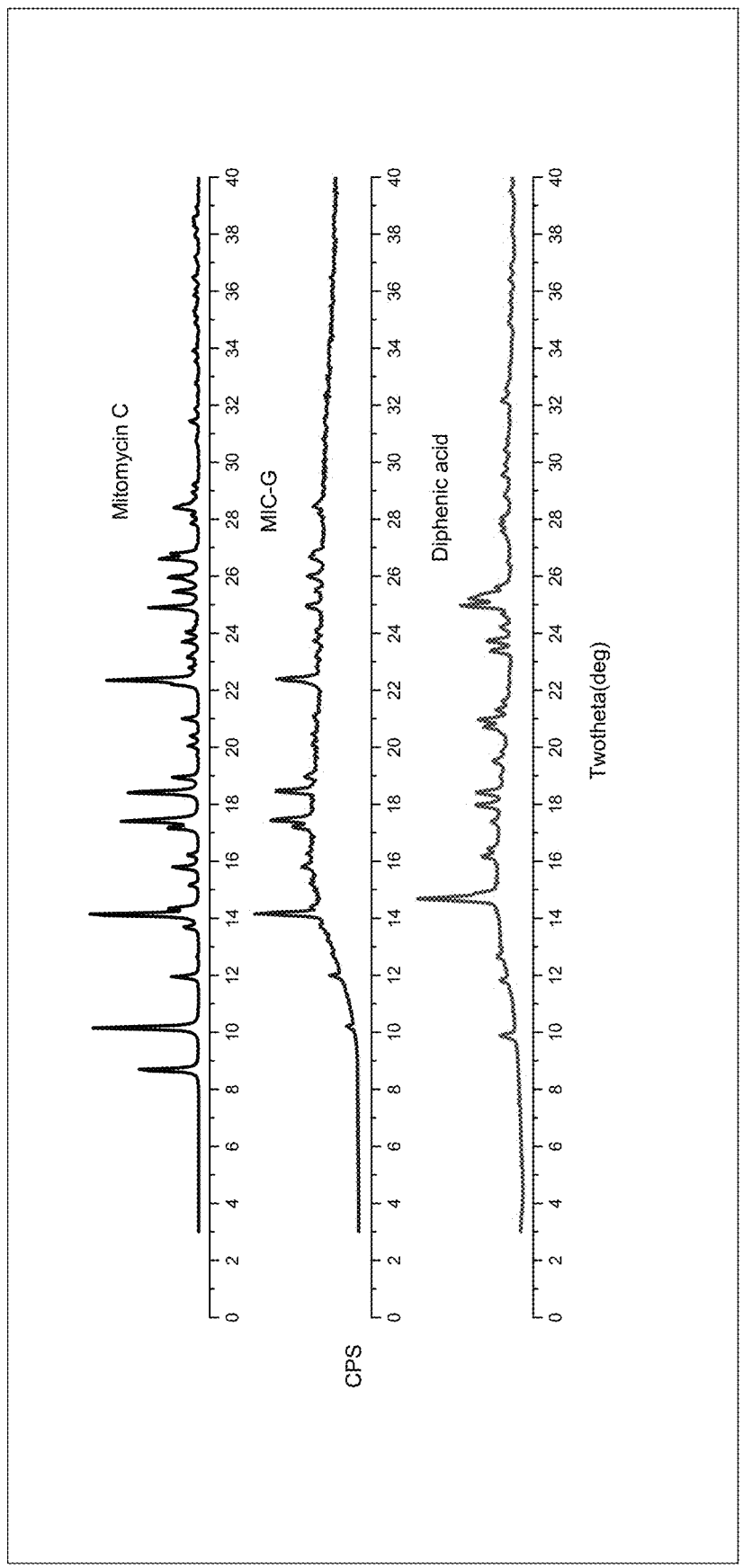
Figure 1. Mitomycin C:diphenic acid PXRD diffractogram

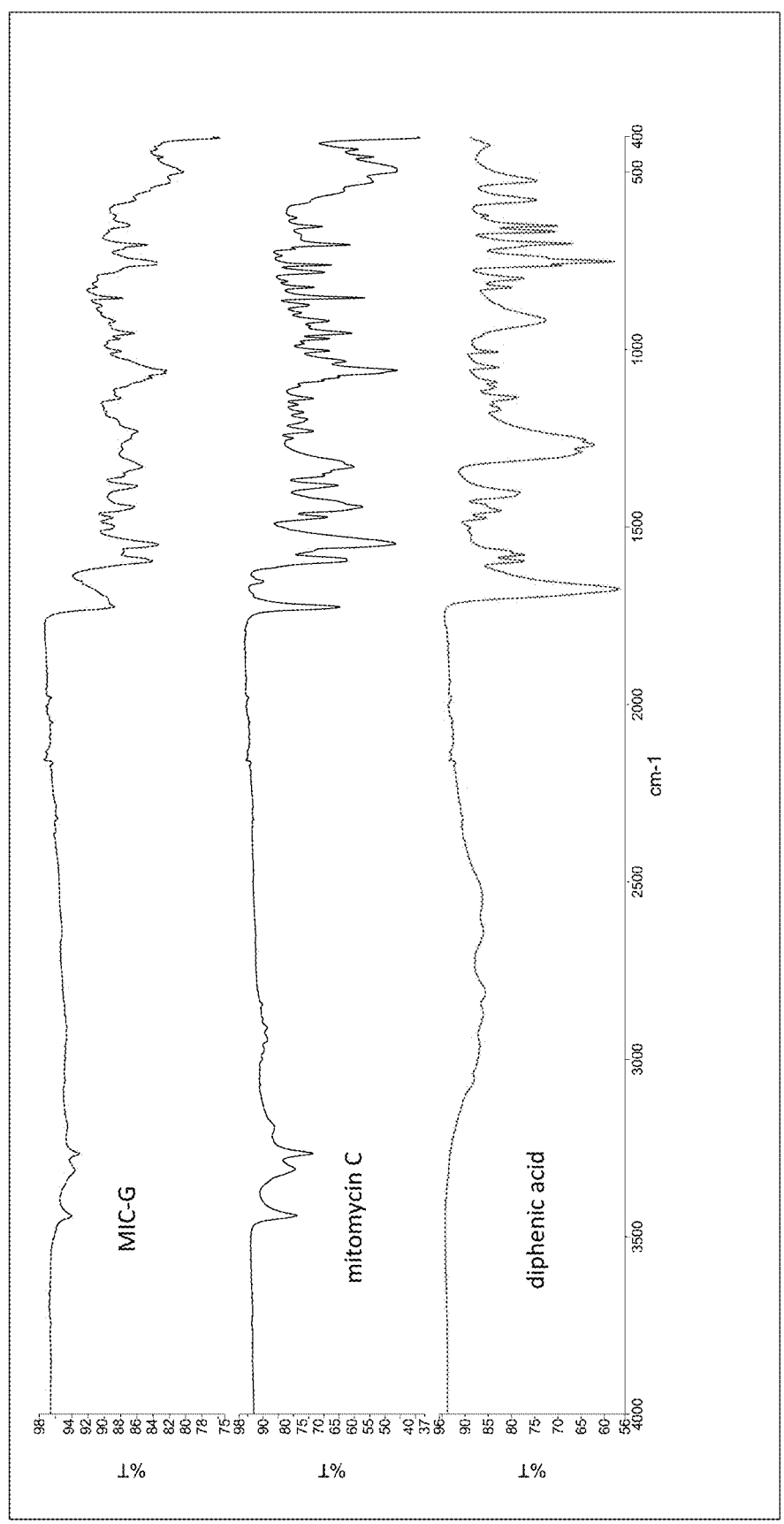
Figure 2. Mitomycin C:diphenic acid FTIR data

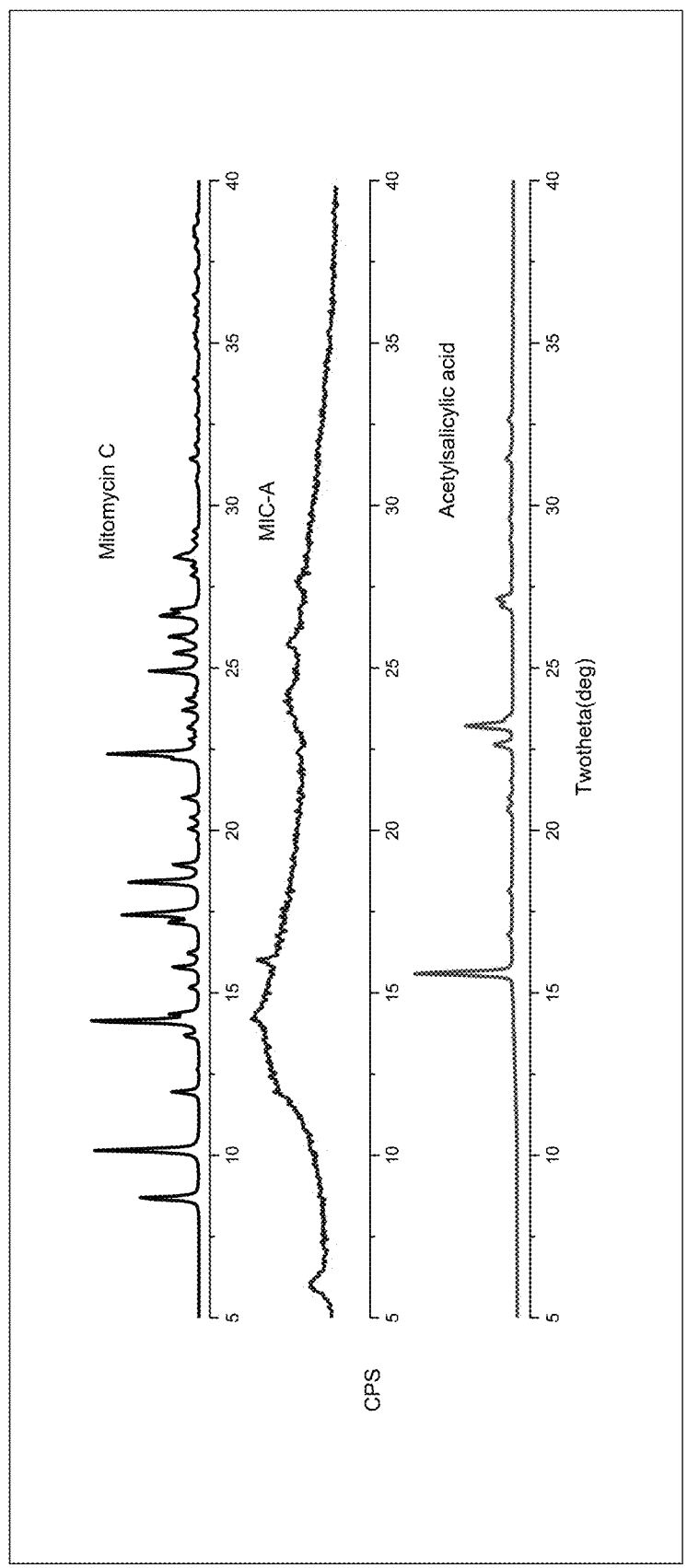
Figure 3. Mitomycin C:acetylsalicylic acid PXRD diffractogram

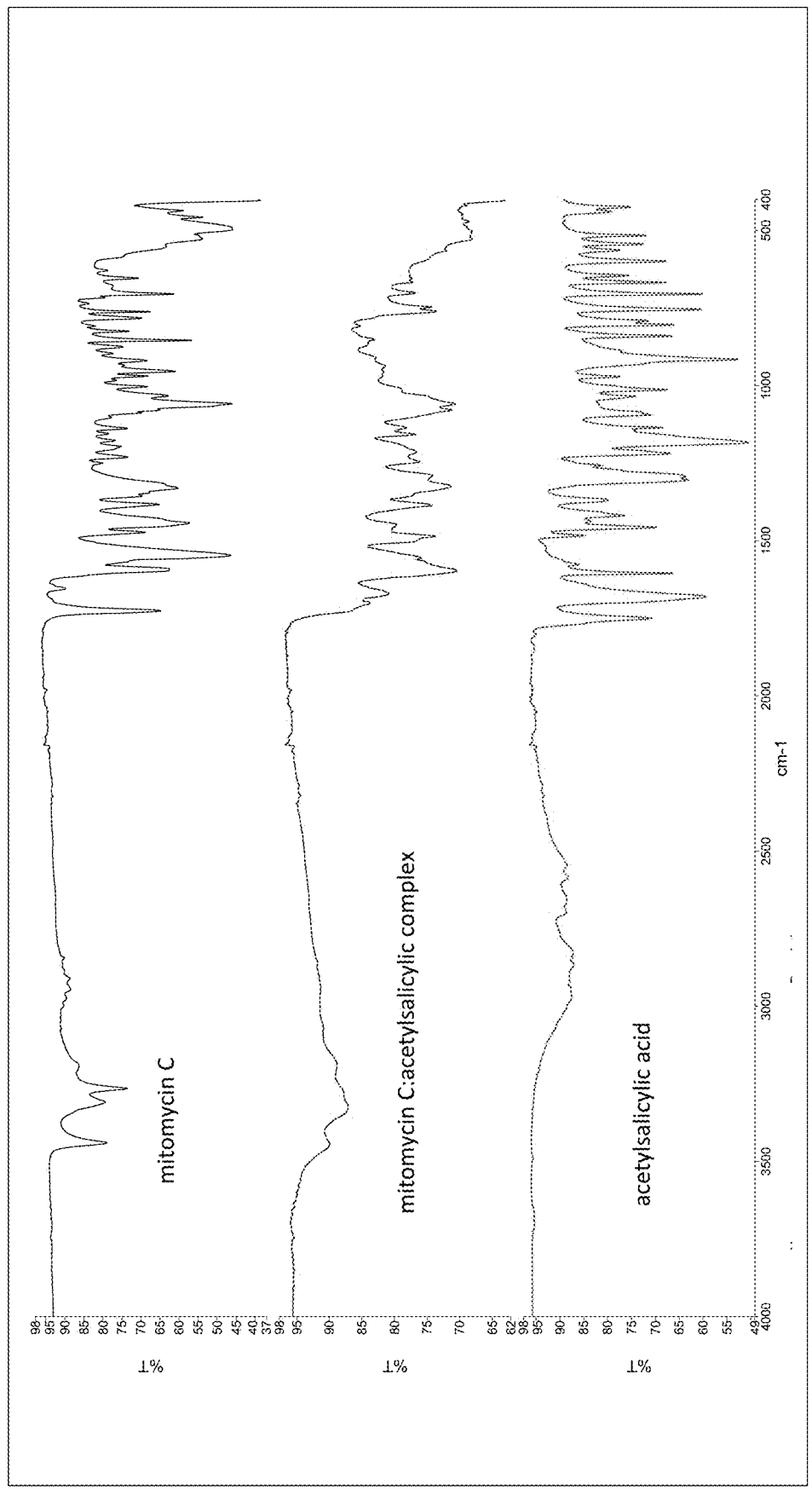
Figure 4. Mitomycin C:acetylsalicylic acid FTIR data

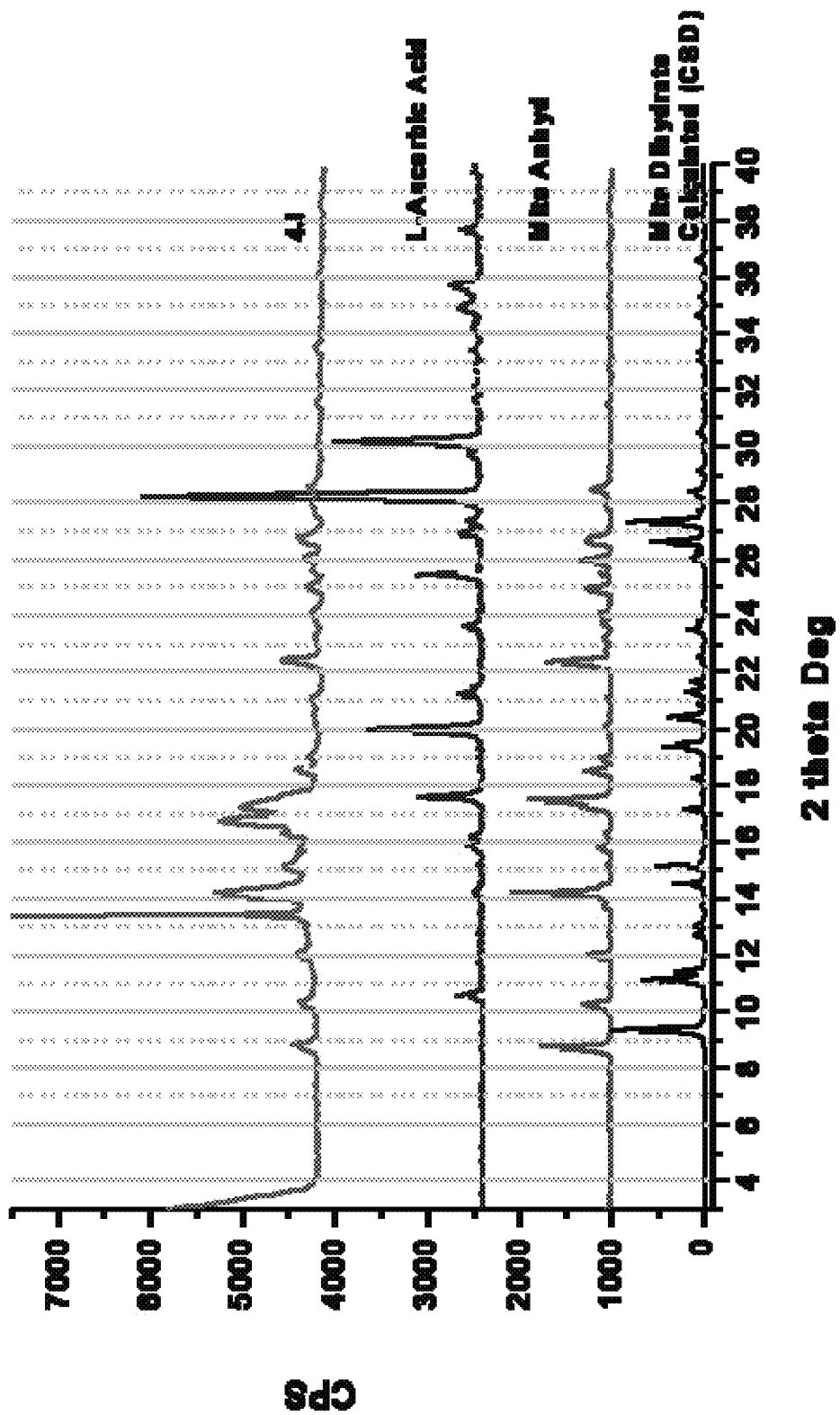
Figure 5. Mitomycin C:L-ascorbic acid PXRD diffractogram (top profile)

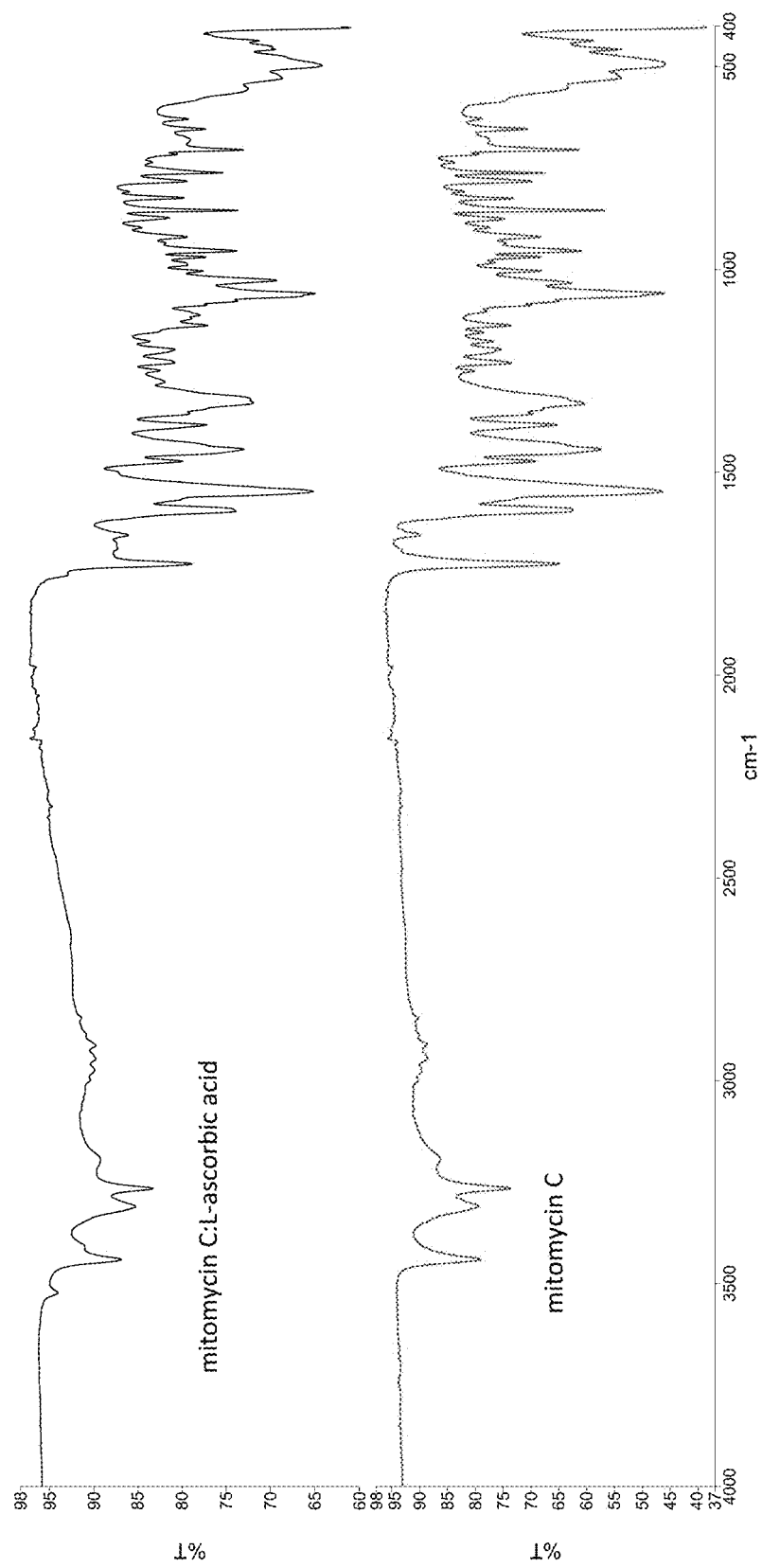
Figure 6. Mitomycin C:L-ascorbic acid FTIR data

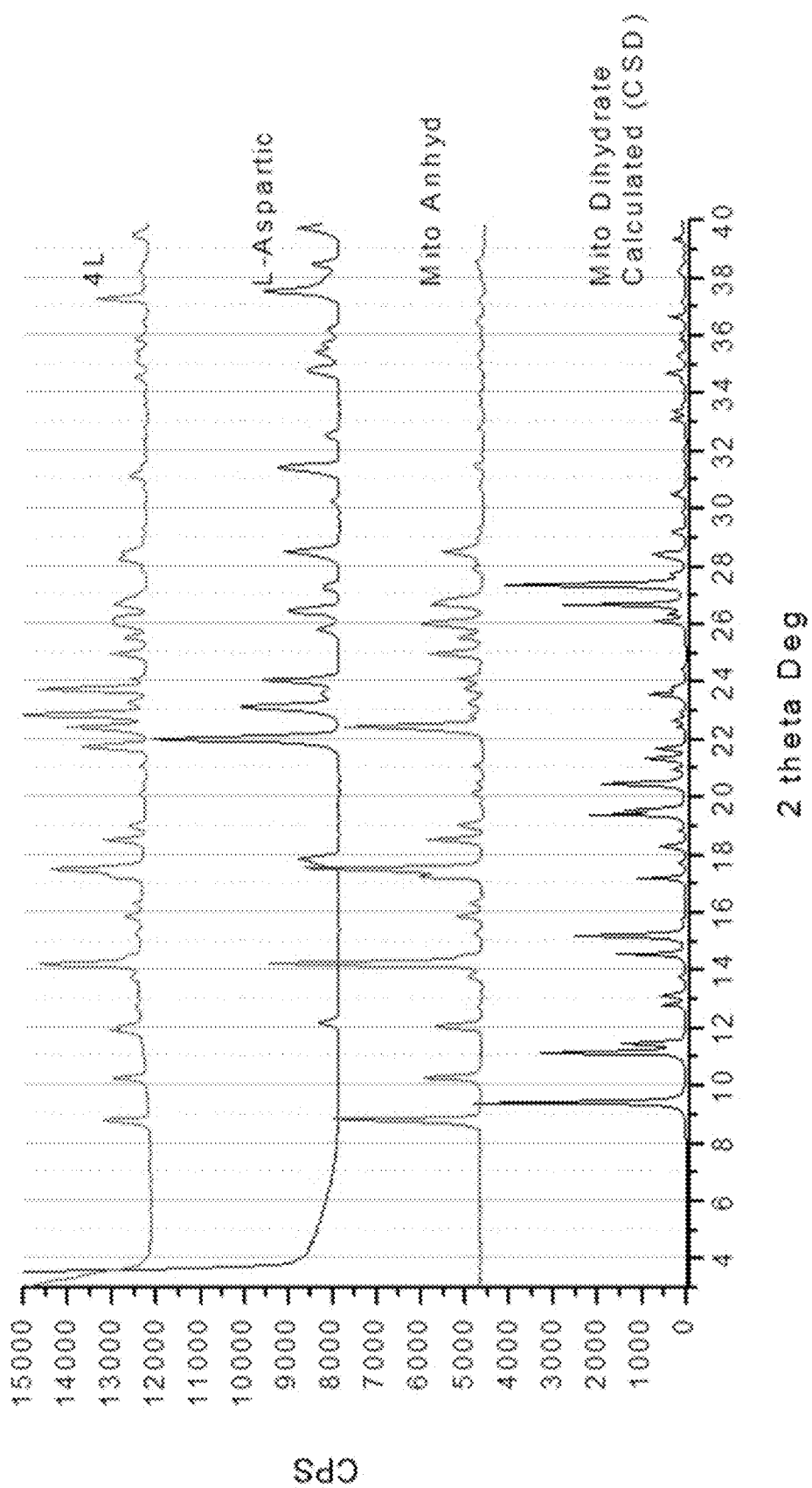
Figure 7. Mitomycin C:L-aspartic acid PXRD diffractogram (top profile)

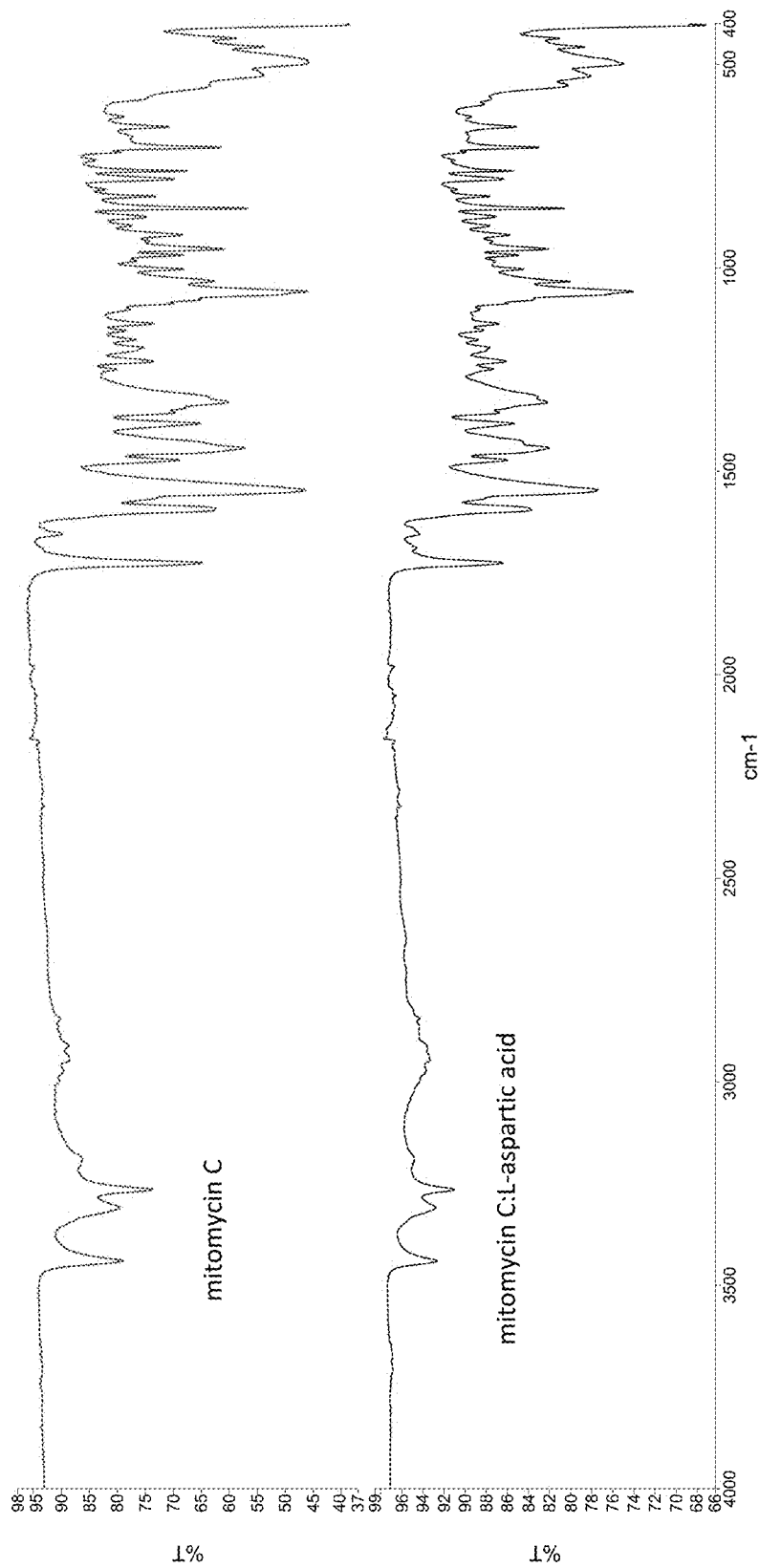
Figure 8. Mitomycin C:L-aspartic acid FTIR data

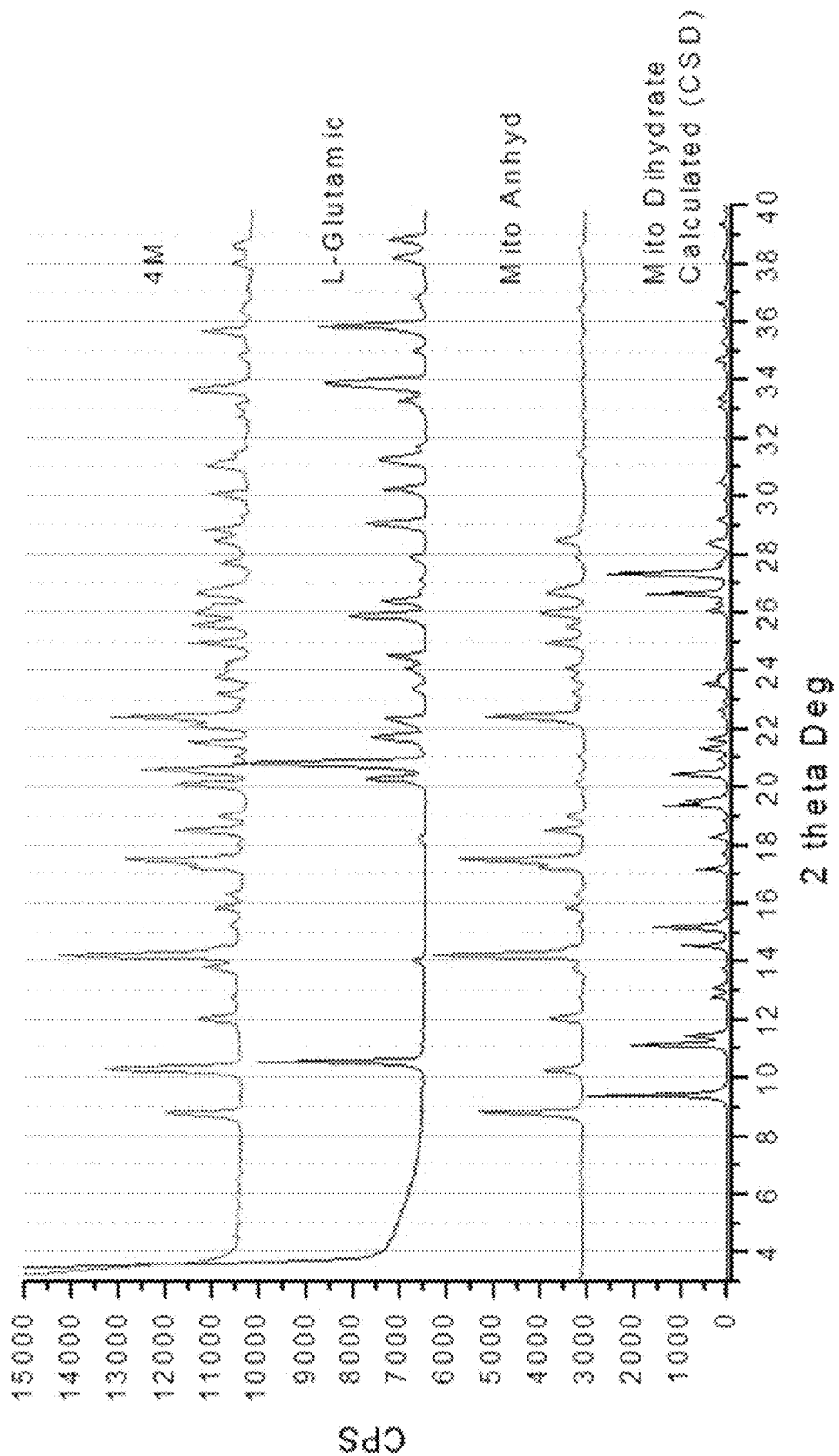
Figure 9. Mitomycin C:L-glutamic acid PXRD diffractogram (top profile)

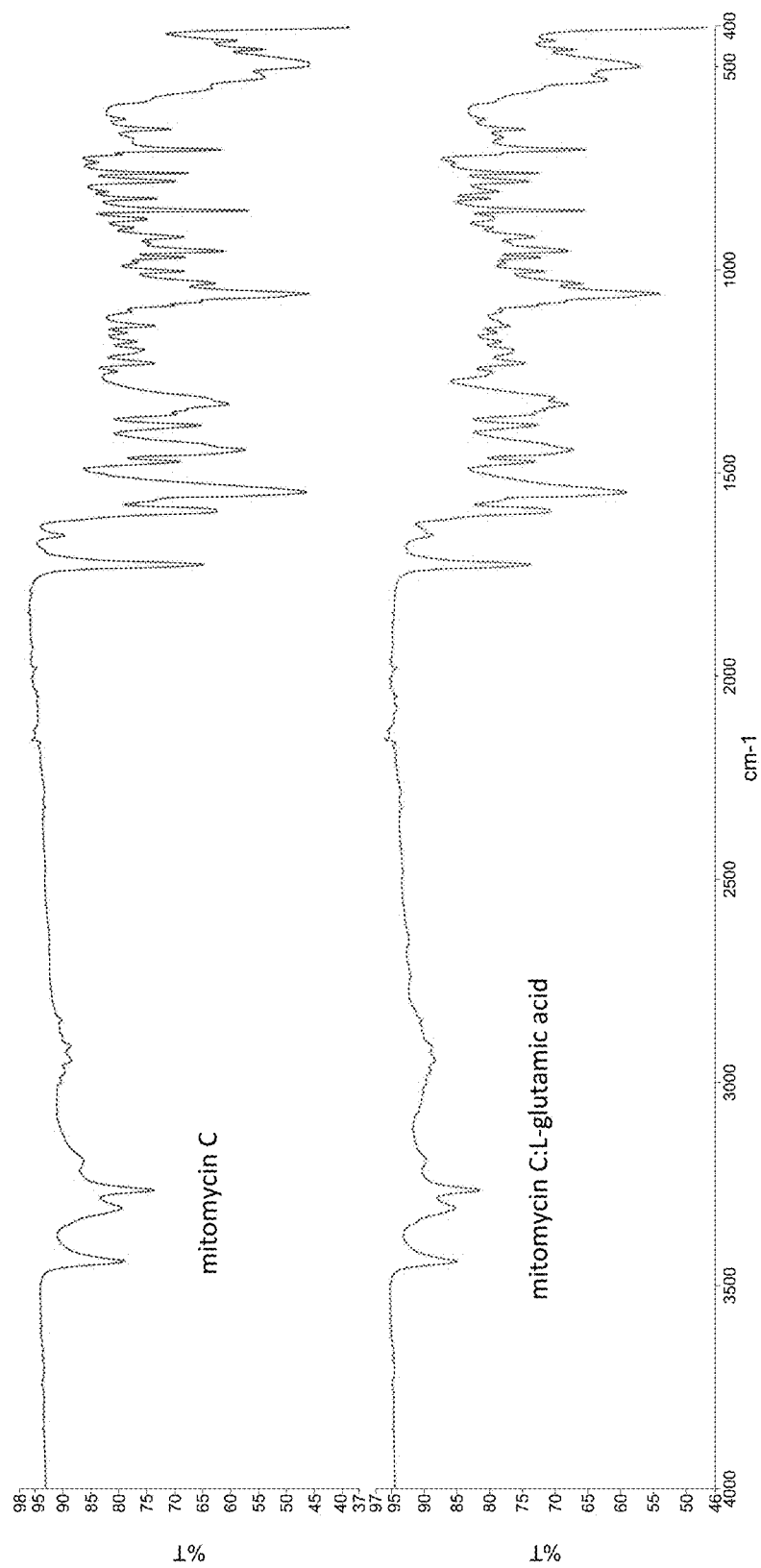
Figure 10. Mitomycin C:L-glutamic acid FTIR data

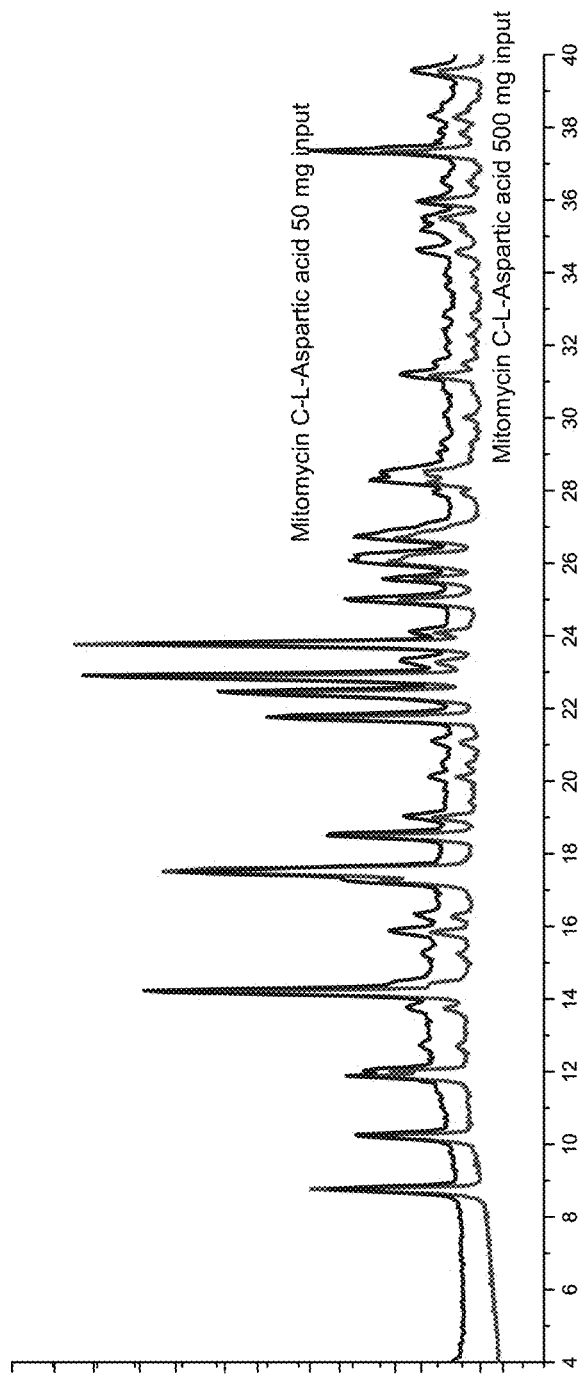
Figure 11. PXRD diffractogram of mitomycin C:L-aspartic acid scaled up experiment

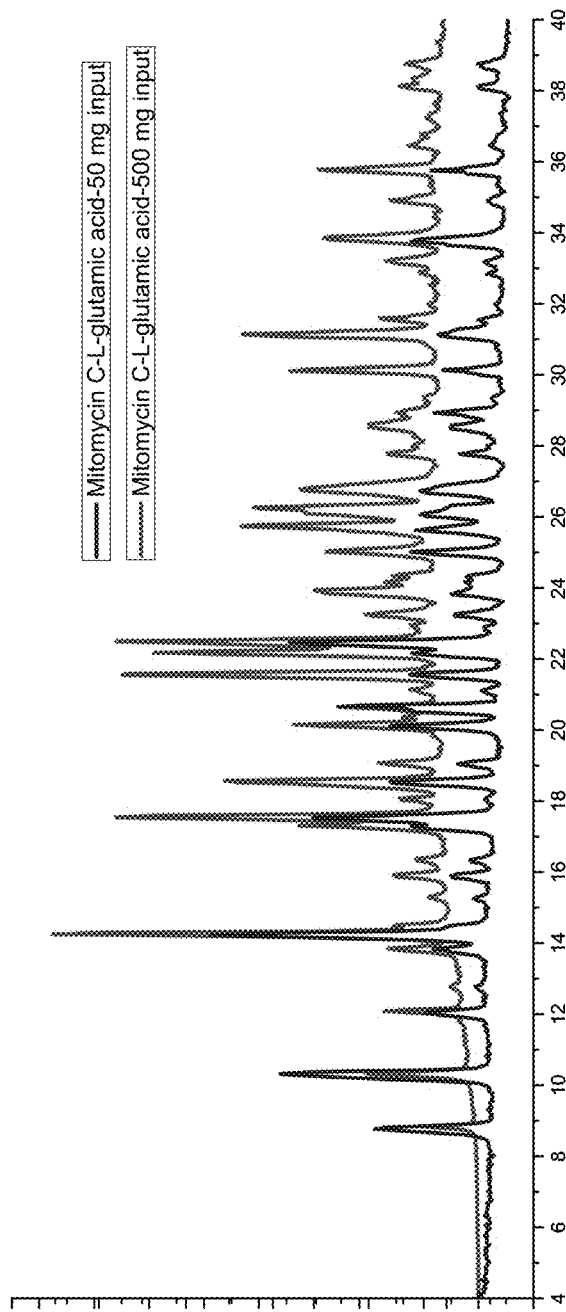
Figure 12. PXRD diffractogram of mitomycin C:L-glutamic acid scaled up experiment.

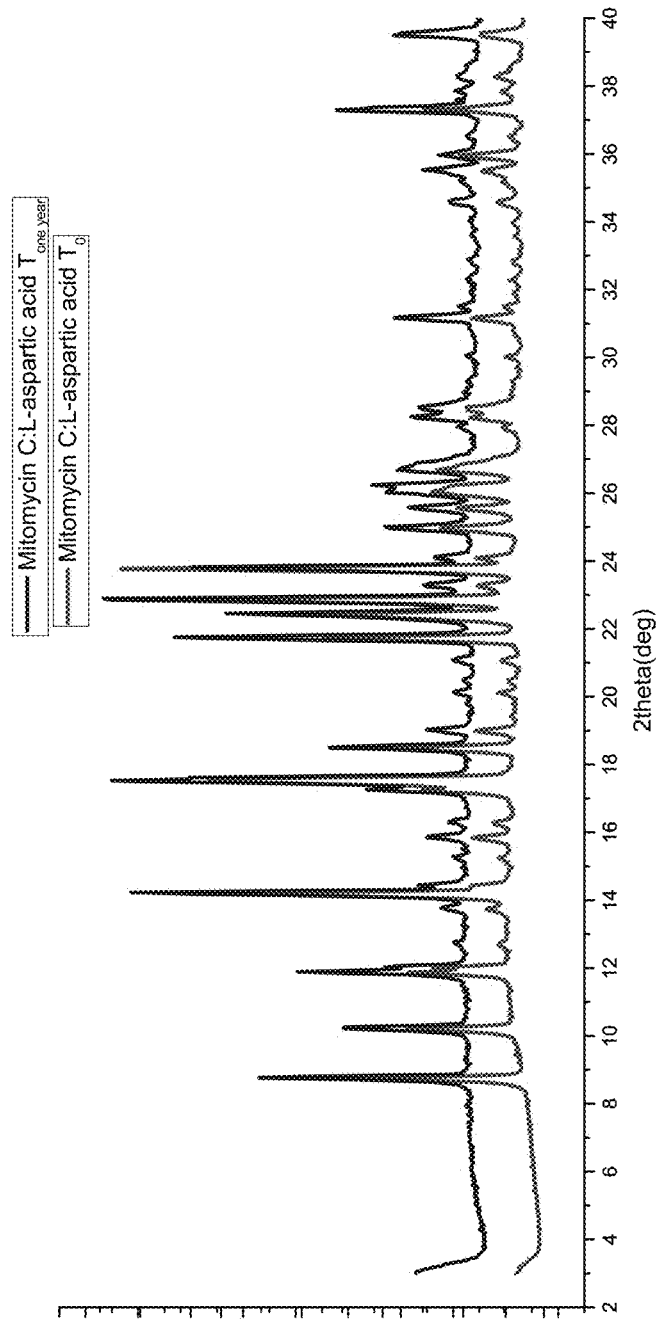
Figure 13. PXRD profile of mitomycin C:L-aspartic acid after one year of accelerated stability testing

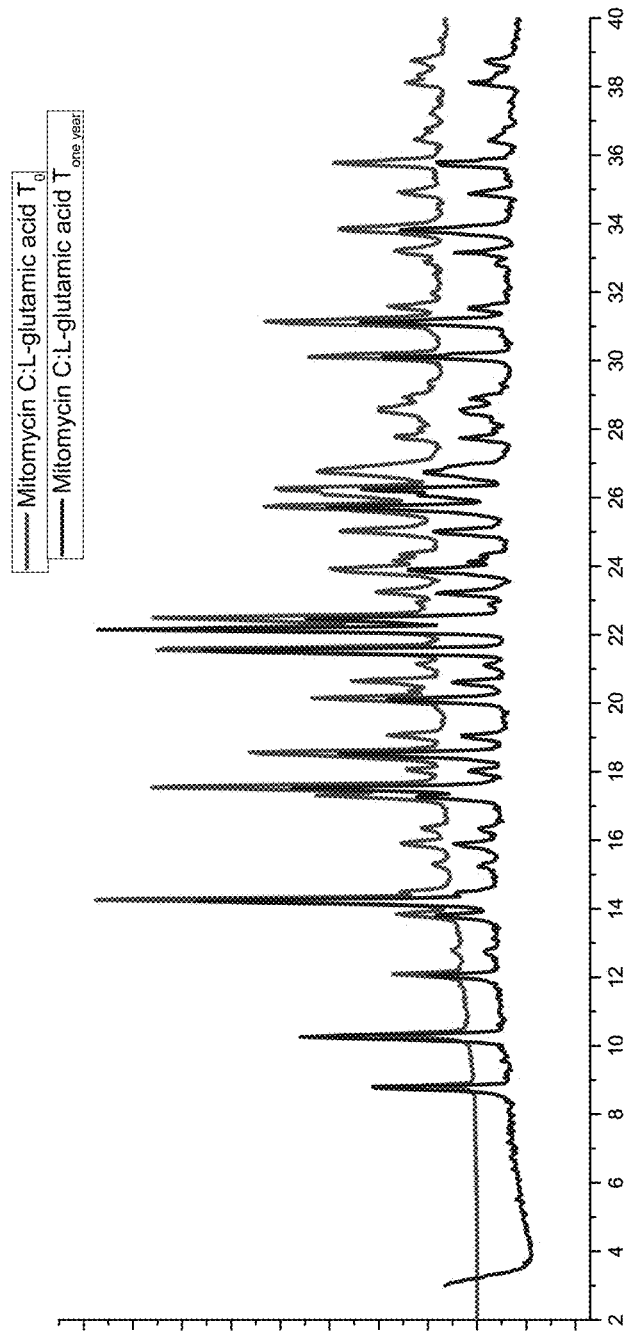
Figure 14. PXRD profile of mitomycin C:L-glutamic acid after one year of accelerated stability studies

CRYSTALLINE FORMS OF MITOMYCIN C FOR TREATMENT OF CANCER

CROSS-REFERENCE TO RELATED APPLICATIONS

This application claims priority to U.S. Provisional Application No. 62/629,888, filed Feb. 13, 2018, which is incorporated herein by reference.

FIELD OF THE INVENTION

This disclosure pertains to novel crystalline forms of mitomycin C and pharmaceutical compositions comprising the same. It can be used for the safe and effective treatment of human or warm-blooded mammal diseases including a variety of cancers not limited to drug resistant cancers, and used as a radio sensitizer. Also, mitomycin is used as a chemotherapeutic agent in glaucoma surgery, as an antifibrotic agent for strabismus surgery, as well as in esophageal and tracheal stenosis. The novel forms include but are not limited to cocrystals, salts, solvates of salts, and mixtures thereof. Methods for the preparation of and pharmaceutical compositions suitable for drug delivery systems that include one or more of these new forms are also disclosed.

BACKGROUND OF THE INVENTION

Mitomycin C (formula I) is classified as an "antitumor antibiotic" drug and was discovered by Japanese microbiologists in 1950s in fermentation cultures of steptomyces caespitous (Szybalski et al. (1964) *Feder. Proc.* 23:946-957). Since then it has obtained a great attention in both preclinical and clinical studies. Mitomycin C shows specific biological effects in mammalian cells including, selective inhibition of DNA synthesis, chromosome breakage, sister chromatid exchange, induction of the DNA repair (SOS response) in bacteria and mutagenesis (Tomasz (1995) *Chemistry and Biology* 2:575-579). Due to the antitumor activity of mitomycin C it is used as a chemotherapeutic agent, given intravenously to treat upper gastrointestinal cancer, anal cancer, breast cancer and as well as by bladder instillation for superficial bladder tumors. In addition, mitomycin C is used topically particularly for bladder cancers and intraperitoneal tumours. It is now well known that a single instillation of this agent within 6 hours of bladder tumor resection can prevent recurrence. One of the major problems of current chemotherapeutics is that they kill bulk of the tumor cells, whereas tumor initiating cancer cells, cancer stem cells escape the drug and develop resistance and they are responsible for tumor recurrence. There is a dire need to discover drugs that kill cancer stem cells in addition to cancer cell.

Furthermore, mitomycin c was shown to reduce fibrosis in strabismus surgery (Kersey et al. (2008) *Strabismus.* pp. 116-118). Also, in eye surgery where mitomycin C 0.02% is applied topically to prevent scarring during glaucoma filtering surgery, and to prevent haze after PRK or LASIK surgery (Abdulaal et al. (2015) *J Refract Surg.* 1:48-52). Moreover, in esophageal and tracheal stenosis, application of mitomycin C onto the mucosa immediately following dilatation decreases re-stenosis by decreasing the production of fibroblasts and scar tissue (Daher Pet al. (2007) *J Pediatr Surg.* 42(9):E9-11).

The empirical formula is $C_{15}H_{18}N_4O_5$, IUPAC name as [(4S,6S,7R,8S)-11-amino-7-methoxy-12-methyl-10,13-dioxo-2,5-diazatetracyclo[7.4.0.0$^{2,7}$.0$^{4,6}$]trideca-1(9),11-dien-8-yl]methyl carbamate and the structural formula maintain a unique structure by arranging quinone, aziridine and carbamate functions around a pyrolo[1,2-a] indole nucleus (Verweij et al. (1990) *Anti-Cancer Drugs* 1:5-13).

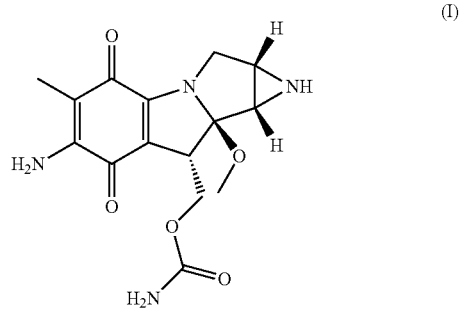 [SMILES: CO[C@@]12[C@H](COC(N)=O)C3=C(C(=O)C(C)=C(N)C3=O)N1C[C@@H]1N[C@@H]12]

(I)

Mitomycin C has a water solubility of 0.5 mg/mL with a pH of 6-7.5. Mitomycin C undergoes rapid degradation in acidic solutions with pH<6 and has a 0.1 mg/mL solubility in ethanol and ~20 mg/mL in DMSO and DMF (Caymen MSDS). Due to the light sensitivity mitomycin C need to be stored in light-resistant containers.

Mitomycin C was approved by FDA in 2002 to be used alone or with other drugs to treat gastric (stomach) and pancreatic adenocarcinoma that is locally advanced or has metastasized. It is used in patients whose disease has not gotten better with other types of treatment. Mitomycin C is administered as an injection or infusion in to the vain. Currently there is no pill form for this drug and referred as a vesicant which can cause extensive tissue damage and blistering if escapes from the vein, therefore need only to be handled by well-trained personals.

Mitomycin C has an enhanced activity in hypoxic environments and hence has a great potential for loco-regional treatment of solid tumors since a significant percentage of viable cancer cells within a solid tumor can be hypoxic. However, mitomycin C is associated with a number of acute and chronic toxicities, such as irreversible myelosuppression and hemolytic-uremic syndrome, which limit its clinical application (Hou et al. (2009) *Nanoscale Res. Lett.* 4:732-737). Mild and infrequent anorexia, nausea, vomiting and diarrhea are other common side effects caused by the use of mitomycin C. High doses of mitomycin C (60 mg per dose) also may result in lethal veno-occlusive liver diseases (Lazarus et al. (1982) *Cancer* 49:1789-1795). Therefore, there is an obvious need for the development of new forms of mitomycin C with the retention of antitumor activity and diminishing the side effects.

There is very little information available on the generation and characterization of different solid forms of mitomycin C though the crystal structure of pure mitomycin C and hydrates are published in the Cambridge Structural Database (CSD February 2017 update) (Kartha et al. (1979) *ACA Ser.* 2, 6:69a; Ogawa et al. (1979) *Bull. Chem. Soc. Jpn.* 52:2334; Arora (1979) *Life Sci.* 24:1519).

No attempt has been made prior to this invention in designing molecular complexes of mitomycin and such a design will be beneficial in altering the physiochemical properties of the parent drug such as melting point, aqueous solubility, rate of dissolution and permeability. To the best of our knowledge, this is a first attempt to use molecular design to obtain novel solid forms of this anticancer medication in an attempt to improve its physiochemical properties and potentially its clinical profile.

SUMMARY OF THE INVENTION

The present disclosure is directed towards generating new forms of mitomycin C that have improved physicochemical characteristics. One aspect of the present disclosure includes novel neutral and ionic molecular complexes of mitomycin C that includes cocrystals, salts, and solvates (e.g., hydrates and mixed solvates as well as solvates of salts), and mixtures containing such materials. In addition, the disclosure further includes methods for the preparation of such complexes.

The disclosure further includes compositions of molecular complexes of mitomycin C suitable for incorporation in a pharmaceutical dosage form. Specific molecular complexes pertaining to the disclosure include, but are not limited to, complexes of mitomycin C and acetylsalicylic acid, diphenic acid, L-aspartic, L-glutamic, and L-ascorbic acids. Obvious variants of the disclosed mitomycin C forms in the specification, drawings, and examples will be readily apparent to the person of ordinary skill in the art having the present disclosure, and such variants are considered to be a part of the current invention.

The disclosure also includes results of characterization of the new molecular complexes by PXRD and FTIR confirming their novelty compared with that of their parent molecule and the conformer.

The foregoing and other features and advantages of the disclosed technology will become more apparent from the following detailed description, which proceeds with reference to the accompanying drawings. Such description is meant to be illustrative, but not limiting, of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1. PXRD diffractograms of novel form mitomycin C:diphenic acid (middle profile).

FIG. 2. FTIR spectrum of novel form mitomycin C:diphenic acid (top spectrum).

FIG. 3. PXRD diffractograms of novel form mitomycin C:acetylsalicylic acid (middle profile).

FIG. 4. FTIR spectrum of novel form mitomycin C:acetylsalicylic acid (middle spectrum).

FIG. 5. PXRD diffractograms of novel form mitomycin C:L-ascorbic acid (top profile 4J is the mitomycin:L-ascorbic acid novel form).

FIG. 6. FTIR spectrum of novel form mitomycin C:L-ascorbic acid (top spectrum).

FIG. 7. PXRD diffractograms of novel form mitomycin C:L-aspartic acid (top profile 4L is the mitomycin:L-aspartic acid novel form).

FIG. 8. FTIR spectrum of novel form mitomycin C:L-aspartic acid (bottom spectrum).

FIG. 9. PXRD diffractograms of novel form mitomycin C:L-glutamic acid (top profile 4M is the mitomycin:L-Glutaric acid novel form).

FIG. 10. FTIR spectrum of novel form mitomycin C:L-glutamic acid (bottom spectrum).

FIG. 11. PXRD diffractogram of mitomycin C:L-aspartic acid scaled up experiment.

FIG. 12. PXRD diffractogram of mitomycin C:L-glutamic acid scaled up experiment.

FIG. 13. PXRD diffractogram of mitomycin C:L-aspartic acid after one year of accelerated stability testing.

FIG. 14. PXRD spectrums of mitomycin C:L-glutamic acid after one year of accelerated stability testing.

DETAILED DESCRIPTION OF THE INVENTION

In general, active pharmaceutical ingredients (APIs) in pharmaceutical compositions can be prepared in a variety of different forms. Such compounds can be prepared to have a variety of different chemical forms including chemical derivatives, solvates, hydrates, cocrystals, and/or salts. Such compounds can also be prepared to have different physical forms. For example, they may be amorphous, may have different crystalline polymorphs, or may exist in different solvated or hydrated states. The discovery of new forms of a pharmaceutically useful compound provides an opportunity to improve the performance characteristics of a pharmaceutical product. Additionally, it expands the array of resources available for designing, for example, a pharmaceutical dosage form of a drug with a targeted release profile or other desired characteristics.

A specific characteristic that can be targeted includes the crystal form of an API. By altering the crystal form, it therefore becomes possible to vary the physical properties of the target molecule. For example, crystalline polymorphs typically have different aqueous solubility from one another, such that a more thermodynamically stable polymorph is less soluble than a less thermodynamically stable polymorph. In addition to water solubility, pharmaceutical polymorphs can also differ in properties such as rate of dissolution, shelf-life, bioavailability, morphology, vapor pressure, density, color, and compressibility. Accordingly, it is desirable to enhance the properties of an active pharmaceutical compound by forming molecular complexes such as a cocrystal, a salt, a solvate or hydrate with respect to aqueous solubility, rate of dissolution, bioavailability, Cmax, Tmax, physicochemical stability, down-stream processibility (e.g., flowability compressibility, degree of brittleness, particle size manipulation), crystallization of amorphous compounds, decrease in polymorphic form diversity, toxicity, taste, production costs, and manufacturing methods.

During the development of drugs, it is frequently advantageous to have novel crystalline forms of such drug materials that possess improved properties, including increased aqueous solubility and stability. It is also desirable, in general, to increase the dissolution rate of such solid forms and potentially increase their bioavailability if used in an oral delivery setting. This also applies to the development of novel forms of mitomycin C which, when administered orally to a subject could achieve a greater or similar bioavailability and pK profile when compared to an IV or other formulations on a dose-for-dose basis.

Cocrystals, salts, solvates, and hydrates of mitomycin C of the present invention could give rise to improved properties. For example, a new mitomycin C form is particularly advantageous if it can improve the oral bioavailability or the clinical profile of the IV version by cutting the dose for instance. A number of novel mitomycin C forms have been synthesized, characterized, and disclosed herein.

The present invention further includes compositions of molecular complexes of mitomycin C suitable for incorporation in a pharmaceutical dosage form. Specific molecular complexes pertaining to the disclosure include, but are not limited to, complexes of mitomycin C and diphenic acid, acetylsalicylic acid, L-ascorbic acid, L-aspartic acid, and L-glutamic acid, which are capable of complexing through solvent evaporation of their solution in single or mixed solvent systems, and slurry suspension, In one aspect, the invention provides for a molecular complex of mitomycin C and a former selected from the group consisting of: diphenic acid, acetylsalicylic acid, L-ascorbic acid, L-aspartic acid, and L-glutamic acid. In one embodiment, the molecular complex is a crystalline form of mitomycin C and a former selected from the group consisting of: diphenic acid, acetylsalicylic acid, L-ascorbic acid, L-aspartic acid, and L-glutamic acid. In one embodiment, the crystalline form is a cocrystal of mitomycin C and a cocrystal former selected from the group consisting of: diphenic acid, acetylsalicylic acid, L-ascorbic acid, L-aspartic acid, and L-glutamic acid. Crystalline forms between mitomycin C and a former, e.g., cocrystal former, are denoted using a ":" between mitomycin C and the name of the former, i.e., mitomycin C:"former".

In one embodiment, the crystalline form is a mitomycin C:diphenic acid crystalline form. In one embodiment, the crystalline form of mitomycin C:diphenic acid is a 1:1 complex. In another embodiment, the mitomycin C:diphenic acid crystalline form is a cocrystal. In one embodiment, the mitomycin C:diphenic acid crystalline form is characterized by a powder X-ray diffraction pattern comprising a powder X-ray diffraction peak selected from about 14.0, 17.0, 18.5, or 22.5° 2θ±0.2° 2θ. In another embodiment, the mitomycin C:diphenic acid crystalline form is characterized by a powder X-ray diffraction pattern comprising a powder X-ray diffraction peak at about 14.0° 2θ±0.2° 2θ. In another embodiment, the mitomycin C:diphenic acid crystalline form is characterized by a powder X-ray diffraction pattern comprising a powder X-ray diffraction peak at about 17.0° 2θ±0.2° 2θ. In another embodiment, the mitomycin C:diphenic acid crystalline form is characterized by a powder X-ray diffraction pattern comprising a powder X-ray diffraction peak at about 18.5° 2θ±0.2° 2θ. In another embodiment, the mitomycin C:diphenic acid crystalline form is characterized by a powder X-ray diffraction pattern comprising a powder X-ray diffraction peak at about 22.5° 2θ±0.2° 2θ. In another embodiment, the mitomycin C:diphenic acid crystalline form is characterized by a powder X-ray diffraction pattern comprising any two powder X-ray diffraction peaks selected from about 14.0, 17.0, 18.5, or 22.5° 2θ±0.2° 2θ. In another embodiment, the mitomycin C:diphenic acid crystalline form is characterized by a powder X-ray diffraction pattern comprising any three powder X-ray diffraction peaks selected from about 14.0, 17.0, 18.5, or 22.5° 2θ±0.2° 2θ. In another embodiment, the mitomycin C:diphenic acid crystalline form is characterized by a powder X-ray diffraction pattern comprising powder X-ray diffraction peaks at about 14.0, 17.0, 18.5, and 22.5° 2θ±0.2° 2θ.

In one embodiment, the crystalline form is a mitomycin C:acetylsalicylic acid crystalline form. In another embodiment, the mitomycin C:acetylsalicylic acid crystalline form is a cocrystal. In another embodiment, the mitomycin C:acetylsalicylic acid crystalline form is characterized by a powder X-ray diffraction pattern comprising a powder X-ray diffraction peak selected from about 5.0, 16.0, 26.0, or 28.0° 2θ±0.2° 2θ. In another embodiment, the mitomycin C:acetylsalicylic acid crystalline form is characterized by a powder X-ray diffraction pattern comprising a powder X-ray diffraction peak at about 5.0° 2θ±0.2° 2θ. In another embodiment, the mitomycin C:acetylsalicylic acid crystalline form is characterized by a powder X-ray diffraction pattern comprising a powder X-ray diffraction peak at about 16.0° 2θ±0.2° 2θ. In another embodiment, the mitomycin C:acetylsalicylic acid crystalline form is characterized by a powder X-ray diffraction pattern comprising a powder X-ray diffraction peak at about 26.0° 2θ±0.2° 2θ. In another embodiment, the mitomycin C:acetylsalicylic acid crystalline form is characterized by a powder X-ray diffraction pattern comprising a powder X-ray diffraction peak at about 28.0° 2θ±0.2° 2θ. In another embodiment, the mitomycin C:acetylsalicylic acid crystalline form is characterized by a powder X-ray diffraction pattern comprising any two powder X-ray diffraction peaks selected from about 5.0, 16.0, 26.0, or 28.0° 2θ±0.2° 2θ. In another embodiment, the mitomycin C:acetylsalicylic acid crystalline form is characterized by a powder X-ray diffraction pattern comprising any three powder X-ray diffraction peaks selected from about 5.0, 16.0, 26.0, or 28.0° 2θ±0.2° 2θ. In another embodiment, the mitomycin C:acetylsalicylic acid crystalline form is characterized by a powder X-ray diffraction pattern comprising powder X-ray diffraction peaks at about 5.0, 16.0, 26.0, and 28.0° 2θ±0.2° 2θ.

In one embodiment, the crystalline form is a mitomycin C:L-ascorbic acid crystalline form. In another embodiment, the mitomycin C:L-ascorbic acid crystalline form is a cocrystal. In another embodiment, the mitomycin C:L-ascorbic acid crystalline form is characterized by a powder X-ray diffraction pattern comprising a powder X-ray diffraction peak at about 9.0, 13.5, 14.5, 16.5, 17.5, or 22.5° 2θ±0.2° 2θ. In another embodiment, the mitomycin C:L-ascorbic acid crystalline form is characterized by a powder X-ray diffraction pattern comprising a powder X-ray diffraction peak at 9.0° 2θ±0.2° 2θ. In another embodiment, the mitomycin C:L-ascorbic acid crystalline form is characterized by a powder X-ray diffraction pattern comprising a powder X-ray diffraction peak at 13.5° 2θ±0.2° 2θ. In another embodiment, the mitomycin C:L-ascorbic acid crystalline form is characterized by a powder X-ray diffraction pattern comprising a powder X-ray diffraction peak at 14.5° 2θ±0.2° 2θ. In another embodiment, the mitomycin C:L-ascorbic acid crystalline form is characterized by a powder X-ray diffraction pattern comprising a powder X-ray diffraction peak at 16.5° 2θ±0.2° 2θ. In another embodiment, the mitomycin C:L-ascorbic acid crystalline form is characterized by a powder X-ray diffraction pattern comprising a powder X-ray diffraction peak at 17.5° 2θ±0.2° 2θ. In another embodiment, the mitomycin C:L-ascorbic acid crystalline form is characterized by a powder X-ray diffraction pattern comprising a powder X-ray diffraction peak at 22.5° 2θ±0.2° 2θ. In another embodiment, the mitomycin C:L-ascorbic acid crystalline form is characterized by a powder X-ray diffraction pattern comprising any two powder X-ray diffraction peaks selected from about 9.0, 13.5, 14.5, 16.5, 17.5, or 22.5° 2θ±0.2° 2θ. In another embodiment, the mitomycin C:L-ascorbic acid crystalline form is characterized by a powder X-ray diffraction pattern comprising any three powder X-ray diffraction peaks selected from about 9.0, 13.5, 14.5, 16.5, 17.5, or 22.5° 2θ±0.2° 2θ. In another embodiment, the mitomycin C:L-ascorbic acid crystalline form is characterized by a powder X-ray diffraction pattern comprising any four powder X-ray diffraction peaks selected from about 9.0, 13.5, 14.5, 16.5, 17.5, or 22.5° 2θ±0.2° 2θ. In another embodiment, the mitomycin C:L-ascorbic acid crystalline form is characterized by a powder X-ray diffraction pattern comprising any five powder X-ray diffraction peaks selected from about 9.0, 13.5, 14.5, 16.5, 17.5, or 22.5° 2θ±0.2° 2θ. In another embodiment, the mitomycin C:L-ascorbic acid crystalline form is characterized by a powder X-ray diffraction pattern comprising powder X-ray diffraction peaks at 9.0, 13.5, 14.5, 16.5, 17.5, and 22.5° 2θ±0.2° 2θ.

In one embodiment, the crystalline form is a mitomycin C:L-aspartic acid crystalline form. In another embodiment, the mitomycin C:L-aspartic acid crystalline form is a cocrystal. In another embodiment, the mitomycin C:L-aspartic acid crystalline form is characterized by a powder X-ray diffraction pattern comprising a powder X-ray diffraction peak at about 8.5, 10.0, 12.0, 14.0, 17.5, 23.0, or 23.5° 2θ±0.2° 2θ. In another embodiment, the mitomycin C:L-aspartic acid crystalline form is characterized by a powder X-ray diffraction pattern comprising a powder X-ray diffraction peak at about 8.5° 2θ±0.2° 2θ. In another embodiment, the mitomycin C:L-aspartic acid crystalline form is characterized by a powder X-ray diffraction pattern comprising a powder X-ray diffraction peak at about 10.0° 2θ±0.2° 2θ. In another embodiment, the mitomycin C:L-aspartic acid crystalline form is characterized by a powder X-ray diffraction pattern comprising a powder X-ray diffraction peak at about 12.0° 2θ±0.2° 2θ. In another embodiment, the mitomycin C:L-aspartic acid crystalline form is characterized by a powder X-ray diffraction pattern comprising a powder X-ray diffraction peak at about 14.0° 2θ±0.2° 2θ. In another embodiment, the mitomycin C:L-aspartic acid crystalline form is characterized by a powder X-ray diffraction pattern comprising a powder X-ray diffraction peak at about 17.5° 2θ±0.2° 2θ. In another embodiment, the mitomycin C:L-aspartic acid crystalline form is characterized by a powder X-ray diffraction pattern comprising a powder X-ray diffraction peak at about 23.0° 2θ±0.2° 2θ. In another embodiment, the mitomycin C:L-aspartic acid crystalline form is characterized by a powder X-ray diffraction pattern comprising a powder X-ray diffraction peak at about 23.5° 2θ±0.2° 2θ. In another embodiment, the mitomycin C:L-aspartic acid crystalline form is characterized by a powder X-ray diffraction pattern comprising any two powder X-ray diffraction peaks selected from about 8.5, 10.0, 12.0, 14.0, 17.5, 23.0, or 23.5° 2θ±0.2° 2θ. In another embodiment, the mitomycin C:L-aspartic acid crystalline form is characterized by a powder X-ray diffraction pattern comprising any three powder X-ray diffraction peaks selected from about 8.5, 10.0, 12.0, 14.0, 17.5, 23.0, or 23.5° 2θ±0.2° 2θ. In another embodiment, the mitomycin C:L-aspartic acid crystalline form is characterized by a powder X-ray diffraction pattern comprising any four powder X-ray diffraction peaks selected from about 8.5, 10.0, 12.0, 14.0, 17.5, 23.0, or 23.5° 2θ±0.2° 2θ. In another embodiment, the mitomycin C:L-aspartic acid crystalline form is characterized by a powder X-ray diffraction pattern comprising any five powder X-ray diffraction peaks selected from about 8.5, 10.0, 12.0, 14.0, 17.5, 23.0, or 23.5° 2θ±0.2° 2θ. In another embodiment, the mitomycin C:L-aspartic acid crystalline form is characterized by a powder X-ray diffraction pattern comprising any six powder X-ray diffraction peaks selected from about 8.5, 10.0, 12.0, 14.0, 17.5, 23.0, or 23.5° 2θ±0.2° 2θ. In another embodiment, the mitomycin C:L-aspartic acid crystalline form is characterized by a powder X-ray diffraction pattern comprising peaks at about 8.5, 10.0, 12.0, 14.0, 17.5, 23.0, and 23.5° 2θ±0.2° 2θ.

In one embodiment, the crystalline form is a mitomycin C:L-glutamic acid crystalline form. In another embodiment, the mitomycin C:L-glutamic acid crystalline form is a cocrystal. In another embodiment, the mitomycin C:L-glutamic acid crystalline form is characterized by a powder X-ray diffraction pattern comprising a powder X-ray diffraction peak at about 8.5, 10.5, 14.0, 17.5, 18.5, or 20.0° 2θ±0.2° 2θ. In another embodiment, the mitomycin C:L-glutamic acid crystalline form is characterized by a powder X-ray diffraction pattern comprising a powder X-ray diffraction peak at about 8.5° 2θ±0.2° 2θ. In another embodiment, the mitomycin C:L-glutamic acid crystalline form is characterized by a powder X-ray diffraction pattern comprising a powder X-ray diffraction peak at about 10.5° 2θ±0.2° 2θ. In another embodiment, the mitomycin C:L-glutamic acid crystalline form is characterized by a powder X-ray diffraction pattern comprising a powder X-ray diffraction peak at about 14.0° 2θ±0.2° 2θ. In another embodiment, the mitomycin C:L-glutamic acid crystalline form is characterized by a powder X-ray diffraction pattern comprising a powder X-ray diffraction peak at about 17.5° 2θ±0.2° 2θ. In another embodiment, the mitomycin C:L-glutamic acid crystalline form is characterized by a powder X-ray diffraction pattern comprising a powder X-ray diffraction peak at about 18.5° 2θ±0.2° 2θ. In another embodiment, the mitomycin C:L-glutamic acid crystalline form is characterized by a powder X-ray diffraction pattern comprising a powder X-ray diffraction peak at about 20.0° 2θ±0.2° 2θ. In another embodiment, the mitomycin C:L-glutamic acid crystalline form is characterized by a powder X-ray diffraction pattern comprising any two powder X-ray diffraction peaks selected from about 8.5, 10.5, 14.0, 17.5, 18.5, or 20.0° 2θ±0.2° 2θ. In another embodiment, the mitomycin C:L-glutamic acid crystalline form is characterized by a powder X-ray diffraction pattern comprising any three powder X-ray diffraction peaks selected from about 8.5, 10.5, 14.0, 17.5, 18.5, or 20.0° 2θ±0.2° 2θ. In another embodiment, the mitomycin C:L-glutamic acid crystalline form is characterized by a powder X-ray diffraction pattern comprising any four powder X-ray diffraction peaks selected from about 8.5, 10.5, 14.0, 17.5, 18.5, or 20.0° 2θ±0.2° 2θ. In another embodiment, the mitomycin C:L-glutamic acid crystalline form is characterized by a powder X-ray diffraction pattern comprising any five powder X-ray diffraction peaks selected from about 8.5, 10.5, 14.0, 17.5, 18.5, or 20.0° 2θ±0.2° 2θ. In another embodiment, the mitomycin C:L-glutamic acid crystalline form is characterized by a powder X-ray diffraction pattern comprising powder X-ray diffraction peaks at about 8.5, 10.5, 14.0, 17.5, 18.5, and 20.0° 2θ±0.2° 2θ.

The present invention includes complexes mitomycin C and diphenic acid, acetylsalicylic acid, L-ascorbic acid, L-aspartic acid, and L-glutamic acid, which are capable of complexing in the solid-state, for example, through dry or solvent-drop grinding, heating or solvent evaporation of their solution in single or mixed solvent systems, slurry suspension, antisolvent, supercritical fluids or other techniques known to a person skilled in the art. Solvents and antisolvents used to make the crystalline forms include acetone, ethanol, methanol, ethylacetate (EtOAc), isopropanol (IP A), or isopropylacetate (IP Ac), diethoxymethane (DEM), Toluene, BuOAc, N-methylpyrrolidone (NMP) and a heptane.

In one embodiment, the invention includes crystalline forms of mitomycin C and diphenic acid, acetylsalicylic acid, L-ascorbic acid, L-aspartic acid, and L-glutamic acid which are capable of complexing through solvent evaporation of their solution in single or mixed solvent systems, and slurry suspension.

In another aspect, the invention provides for a pharmaceutical composition comprising a molecular complex of the present invention. In one embodiment, the molecular complex is a crystalline form. In a further embodiment, the crystalline form is a crystalline form of mitomycin C and diphenic acid, acetylsalicylic acid, L-ascorbic acid, L-aspartic acid, or L-glutamic acid. In another embodiment, the crystalline form is a cocrystal of mitomycin C and diphenic acid, acetylsalicylic acid, L-ascorbic acid, L-aspartic acid, or L-glutamic acid.

The pharmaceutical composition comprises a therapeutically effective amount of at least one of the novel molecular complexes of mitomycin C according to the invention and at least one pharmaceutically acceptable excipient. The term "excipient" refers to a pharmaceutically acceptable, inactive substance used as a carrier for the pharmaceutically active ingredient(s) and includes antiadherents, binders, coatings, disintegrants, fillers, diluents, flavors, bulkants, colours, glidants, dispersing agents, wetting agents, lubricants, preservatives, sorbents and sweeteners. The choice of excipient(s) will depend on factors such as the particular mode of administration and the nature of the dosage form. Solutions or suspensions used for intravenous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A pharmaceutical formulation of the present invention may be in any pharmaceutical dosage form. The pharmaceutical formulation may be, for example, a tablet, capsule, nanoparticulate material, e.g., granulated particulate material or a powder, a lyophilized material for reconstitution, liquid suspension, injectable suspension or solution, suppository, or topical or transdermal preparation or patch. The pharmaceutical formulations generally contain about 1% to about 99% by weight of at least one novel molecular complex of mitomycin C of the invention and 99% to 1% by weight of a suitable pharmaceutical excipient. In one embodiment, the dosage form is an oral dosage form. In another embodiment, the dosage form is a parenteral dosage form. In one embodiment, the pharmaceutical dosage form is a unit dose. The term "unit dose" refers to the amount of API administered to a patient in a single dose.

The novel molecular complexes of mitomycin C are therapeutically useful for the treatment and/or prevention of a disease for which it is indicated, e.g., cancer. Accordingly, in another aspect, the invention also relates a method of treating or preventing a disease for which mitomycin C is indicated, said method comprising the step of administering to a patient in need thereof, a therapeutically effective amount of a pharmaceutical composition of the present invention.

In some embodiments, a pharmaceutical composition of the present invention is delivered to a subject via intratumoral injection. "Intratumoral injection" is a route of administration by which a pharmaceutical composition, is delivered directly to the tumor via an injection device (e.g., needle and syringe). In other embodiments, a pharmaceutical composition of the present invention is delivered to a subject via a parenteral route, an enteral route, or a topical route.

Examples of parental routes the present invention include, without limitation, any one or more of the following: intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal, intracoronary, intracorporus, intracranial, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intraocular, intrasinal, intraspinal, intrasynovial, intratendinous, intratesticular, intrathecal, intrathoracic, intratubular, intratumoral, intratympanic, intrauterine, intravascular, intravenous (bolus or drip), intraventricular, intravesical, and/or subcutaneous.

Enteral routes of administration of the present invention include administration to the gastrointestinal tract via the mouth (oral), stomach (gastric), and rectum (rectal). Gastric administration typically involves the use of a tube through the nasal passage (NG tube) or a tube in the esophagus leading directly to the stomach (PEG tube). Rectal administration typically involves rectal suppositories.

Topical, including transdermal, routes of administration of the present invention include administration to a body surface, such as skin or mucous membranes. Delivery vehicles of the present disclosure may be administered topically (or transdermally) via a cream, foam, gel, lotion or ointment, for example.

As used herein, the terms "treat," "treating," or "treatment" means to alleviate, reduce or abrogate one or more symptoms or characteristics of a disease and may be curative, palliative, prophylactic or slow the progression of the disease. The term "therapeutically effective amount" is intended to mean that amount of drug that will elicit a desired biological or pharmacological response, i.e., an amount sufficient to treat said disease. The term "patient" includes mammals, especially humans. In one embodiment, the patient is a warm-blooded mammal. In another embodiment, the patient is a human. In another embodiment, the patient is a human male. In another embodiment, the patient is a human female.

In one embodiment, the invention provides for a method of treating pre-cancer or cancer comprising the step of administering to a cancer patient a therapeutically effective amount of a pharmaceutical composition of the present invention. The present invention further provides for a medicament comprising a pharmaceutical composition of the present invention for use in treating pre-cancer or cancer.

The dosage may vary depending upon the dosage form employed, sensitivity of the patient, and the route of administration. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

In some embodiments, the cancer is selected from: Wilms' tumor, rhabdomyosarcoma, ovarian cancer (e.g., germ cell), gestational trophoblastic neoplasm, Ewing's sarcoma, metastatic testicular tumors (e.g., nonseminoatous), gestational trophoblastic neoplasm, locally recurrent or locoregional solid tumors (sarcomas, carcinomas and adenocarcinomas), acute myeloid leukemia (AML), prostate cancer, skin cancer, actinic keratosis, Bowen's disease, adjuvant cancer therapy or neoadjuvant cancer therapy. In a preferred embodiment, the cancer is skin cancer, actinic keratosis, or Bowen's disease. In a further embodiment, the skin cancer is selected from the group consisting of: basal cell carcinoma (BCC), squamous cell carcinoma (SCC), and melanoma. In another embodiment, the cancer is prostate cancer. In a further embodiment, the prostate cancer is selected from the group consisting of: acinar adenocarcinoma, ductal adenocarcinoma, transitional cell (or urothelial) cancer, squamous cell cancer, small cell prostate cancer, carcinoid, and sarcoma.

In other embodiments, mitomycin C may be used topically for nan-cancerous diseases. For example, it may be used as a chemotherapeutic agent in glaucoma surgery to prevent scarring during glaucoma filtering surgery. It may also be used to prevent haze after PRK or LASIK. Further, it may be used to reduce fibrosis in strabismus surgery. Additionally, it may be used to decrease re-stenosis by decreasing the production of fibroblasts and scar tissue in esophageal and tracheal stenosis.

EXAMPLES

The techniques and approaches set forth in the present disclosure can further be used by the person of ordinary skill in the art to prepare variants thereof, said variants are considered to be part of the present invention.

Materials used to create the novel forms of the present inventions are commercially available and means to synthesize them as well known. Mitomycin C as a starting material used in all experiments in this disclosure was supplied by AdipoGen Life Sciences, CA, USA, with >98% purity by HPLC. All other pure chemicals (Analytical Grade) were supplied by Sigma-Aldrich and used without further purification.

Analytical techniques used to observe the crystalline forms include powder X-ray diffraction (PXRD) and Fourier transform infrared spectroscopy (FTIR). The particular methodology used in such analytical techniques herein should be viewed as illustrative, and not limiting in the context of data collection.

Powder X-Ray Diffraction (PXRD): All mitomycin C novel molecular complex products were observed by a D-8 Bruker X-ray Powder Diffractometer using Cu Kα (λ=1.540562 Å), 40 kV, 40 mA. The data were collected over an angular range of 3° to 40° 2θ in continuous scan mode at room temperature using a step size of 0.05° 2θ and a scan speed of 6.17°/min.

FTIR analysis was performed on a Perkin Elmer Spectrum 100 FTIR spectrometer equipped with a solid-state ATR accessory.

The following examples illustrate the invention without intending to limit its scope.

Example 1: Preparation of mitomycin C:diphenic Acid Complex 50 mg of mitomycin C and 36 mg of diphenic acid (1:1 molar ratio) was stirred as a slurry in a closed 20 mL glass vial with 1 mL of acetone. After 16-24 hours, stirring was stopped and the mixture was dried at room temperature for another 12-16 hours. The material was stored in a screw cap vial and characterized by PXRD and FTIR corresponding to FIGS. 1 and 2, respectively.

Example 2: Preparation of mitomycin C:acetylsalicylic Acid Complex 50 mg of mitomycin C and 27 mg of acetylsalicylic acid (1:1 molar ratio) was stirred as a slurry in a closed 20 mL borosilicate glass vial with 1 mL of acetone. After 16-24 hours, stirring was stopped and the mixture was dried at room temperature for another 12-16 hours. All materials were stored in a screw cap vials and characterized by PXRD and FTIR corresponding to FIGS. 3 and 4, respectively.

Example 3: Preparation of Mitomycin C:L-ascorbic Acid Complex

Mitomycin C (50 mg) was weighed into a small glass vial and 1 molar equivalent of L-ascorbic acid (57.1 mg) was added followed by the addition of 1 mL acetone and the sample was stirred open until dry, about 12-24 hours. The material was stored for subsequent analysis and characterized by PXRD and FTIR corresponding to FIGS. 5 and 6, respectively.

Example 4: Preparation of Mitomycin C:L-aspartic Acid Complex

Mitomycin C (50 mg) was weighed into a small glass vial and 1 molar equivalent of L-aspartic acid (43.2 mg) was added followed by the addition of 1 mL acetone and the sample was stirred open until dry, about 12-24 hours. The material was stored for subsequent analysis. The material was characterized by PXRD and FTIR corresponding to FIGS. 7 and 8, respectively.

Example 5: Preparation of Mitomycin C:L-glutamic Acid Complex 50 mg of mitomycin C were weighed into a small glass vial and 1 molar equivalent of L-glutamic acid (47.7 mg) is added followed by the addition of 1 mL acetone and the sample was stirred open until dry, about 12-24 hours. The solids gathered were dried and stored in a screw cap vials for subsequent analysis. The material was characterized by PXRD and FTIR corresponding to FIGS. 9 and 10 respectively.

Example 6: Scale Up Experiments

This mg level synthesis was then successfully scaled up to a gram level product to demonstrate scalability. Scale up experiments were carried out successfully for the novel forms to a gram level. Here is data for two selected forms of mitomycin C and L-aspartic and L-glutamic acids molecular complexes.

Both experiments in Example 4 and 5 were scaled by a factor of 10× (i.e., 500 mg of mitomycin c, 432 mg of L-aspartic acid and 477 mg of L-glutamic acid used). A representative sample of each was analyzed using PXRD. Results demonstrate that this is a scalable process with consistent novel forms outcome as shown in FIGS. 11 and 12.

Example 7: Accelerated Stability Studies

Stability studies of the mitomycin C novel forms were conducted using accelerated conditions (75% humidity and 40° C.) of which are obvious to the artisan in the field, for more than one year. Selected data of the novel complexes of mitomycin c:L-aspartic and mitomycin c:L-glutamic acid were both stable for at least year. Samples pulled and analyzed at intervals of three months, six months and twelve months has demonstrated their physical form stability as suggested by the PXRD data of samples after one year of storage under such condition, shown in FIGS. 13 and 14.

What is claimed:

1. A crystalline form of mitomycin C selected from the group consisting of: a mitomycin C:diphenic acid cocrystal, a mitomycin C:acetylsalicylic acid cocrystal, a mitomycin C:L-ascorbic acid cocrystal, a mitomycin C:L-aspartic acid cocrystal, and a mitomycin C:L-glutamic acid cocrystal.

2. The crystalline form of claim 1, wherein said crystalline form is the mitomycin C:diphenic acid cocrystal.

3. The crystalline form of claim 2, wherein said crystalline form is characterized by a powder X-ray diffraction pattern comprising one or more powder X-ray diffraction peaks selected from the group consisting of: about 14.0, 17.0, 18.5, and 22.5° 2θ±0.2° 2θ.

4. The crystalline form of claim 1, wherein said crystalline form is the mitomycin C:acetylsalicylic acid cocrystal.

5. The crystalline form of claim 4, wherein said crystalline form is characterized by a powder X-ray diffraction pattern comprising one or more powder X-ray diffraction peaks selected from the group consisting of: about 5.0, 16.0, 26.0, and 28.0° 2θ±0.2° 2θ.

6. The crystalline form of claim 1, wherein said crystalline form is the mitomycin C:L-ascorbic acid cocrystal.

7. The crystalline form of claim 6, wherein said crystalline form is characterized by a powder X-ray diffraction pattern comprising one or more powder X-ray diffraction peaks selected from the group consisting of: about 9.0, 13.5, 14.5, 16.5, 17.5, and 22.5° 2θ±0.2° 2θ.

8. The crystalline form of claim 1, wherein said crystalline form is the mitomycin C:L-aspartic acid cocrystal.

9. The crystalline form of claim 8, wherein said crystalline form is characterized by a powder X-ray diffraction pattern comprising one or more powder X-ray diffraction peaks selected from the group consisting of: about 8.5, 10.0, 12.0, 14.0, 17.5, 23.0, and 23.5° 2θ±0.2° 2θ.

10. The crystalline form of claim 1, wherein said crystalline form is the mitomycin C:glutamic acid cocrystal.

11. The crystalline form of claim 10, wherein said crystalline form is characterized by a powder X-ray diffraction pattern comprising one or more powder X-ray diffraction peaks selected from the group consisting of: about 8.5, 10.5, 14.0, 17.5, 18.5, and 20.0° 2θ±0.2° 2θ.

12. A composition comprising the crystalline form of claim 1.

13. A pharmaceutical composition comprising the crystalline form of claim 1 and at least one pharmaceutically acceptable excipient.

14. The pharmaceutical composition of claim 13, where said pharmaceutical composition is suitable for any drug delivery route.

15. The pharmaceutical composition of claim 14, wherein the pharmaceutical composition is an oral dosage form, a topical dosage form, or an injectable dosage form.

16. The pharmaceutical composition of claim 13, wherein the pharmaceutical composition is a solid dosage form for reconstitution in at least one medium.

17. The pharmaceutical composition of claim 16, wherein the medium is an aqueous or oil based liquid.

18. The pharmaceutical composition of claim 13, wherein the pharmaceutical composition is a unit dose.

19. A method of treating a disease for which mitomycin C is indicated, said method comprising the step of administering to a patient in need thereof, a therapeutically effective amount of a pharmaceutical composition of claim 13.

20. The method of claim 19, wherein said disease is selected from: Wilms' tumor, rhabdomyosarcoma, lung, breast, colon, rectal, head and neck, brain, pancreatic, and ovarian cancers, gestational trophoblastic neoplasm, Ewing's sarcoma, metastatic testicular tumors, locally recurrent or locoregional solid tumors (sarcomas, carcinomas and adenocarcinomas), acute myeloid leukemia (AML), multiple myeloma, Shwachman-Diamond syndrome, prostate cancer, skin cancer, actinic keratosis, Bowen's disease, adjuvant cancer therapy, or neoadjuvant cancer therapy.

21. The method of claim 19, wherein said skin cancer is selected from the group consisting of: basal cell carcinoma (BCC), squamous cell carcinoma (SCC), and melanoma.

22. The method of claim 19, wherein said skin cancer is non-melanoma skin cancer.

23. The method of claim 19, wherein said disease is prostate cancer.

24. The method of claim 23, wherein prostate cancer is selected from the group consisting of: acinar adenocarcinoma, ductal adenocarcinoma, transitional cell (or urothelial) cancer, squamous cell cancer, small cell prostate cancer, carcinoid, and sarcoma.

25. The method of claim 19, wherein the disease is Shwachman-Diamond syndrome.

26. The method of claim 19, wherein said pharmaceutical composition is administered topically or via intratumoral injection.

27. A method of making the crystalline form of claim 1, comprising the steps of: combining mitomycin C and a former selected from the group consisting of: diphenic acid, acetylsalicylic acid, L-ascorbic acid, L-aspartic acid and L-glutamic acid; and forming cocrystals of said mitomycin C and said former.

28. The method of claim 27, wherein said method comprises the step of combining said mitomycin C and said former with a solvent.

29. The method of claim 28, wherein said solvent is selected from the group consisting of: acetone, ethanol, methanol, ethylacetate (EtOAc), isopropanol (IPA), isopropylacetate (IPAc), diethoxymethane (DEM), Toluene, BuOAc, N-methylpyrrolidone (NMP) and a heptane.

30. A pharmaceutical composition comprising the crystalline form of claim 2 and at least one pharmaceutically acceptable excipient.

31. A pharmaceutical composition comprising the crystalline form of claim 10 and at least one pharmaceutically acceptable excipient.

* * * * *